United States Patent [19]

Nomura

[11] Patent Number: 5,501,097
[45] Date of Patent: Mar. 26, 1996

[54] PORTABLE DEVICE FOR MEASURING A COEFFICIENT OF STATIC FRICTION

[75] Inventor: Toshio Nomura, Tokyo, Japan

[73] Assignee: Shinto Scientific Co., Ltd., Tokyo, Japan

[21] Appl. No.: 332,079

[22] Filed: Nov. 1, 1994

[30] Foreign Application Priority Data

Nov. 30, 1993 [JP] Japan .................... 5-323303

[51] Int. Cl.⁶ ............................. G01N 19/02
[52] U.S. Cl. ........................................ 73/9
[58] Field of Search ............................. 73/9, 10

[56] References Cited

U.S. PATENT DOCUMENTS

| | | | |
|---|---|---|---|
| 4,813,266 | 3/1989 | Nash | 73/9 |
| 4,895,015 | 1/1990 | English | 73/9 |
| 5,245,856 | 9/1993 | Pazzaglia et al. | 73/9 |

FOREIGN PATENT DOCUMENTS

| | | | |
|---|---|---|---|
| 390419 | 11/1973 | U.S.S.R. | 73/9 |
| 838527 | 6/1981 | U.S.S.R. | 73/9 |

OTHER PUBLICATIONS

Kurz, "Useful Friction Recorder", American Journal of Physics, vol. 24, No. 3, pp. 174–175, Mar. 1956.

*Primary Examiner*—Thomas P. Noland
*Assistant Examiner*—Daniel S. Larkin
*Attorney, Agent, or Firm*—Wenderoth, Lind & Ponack

[57] ABSTRACT

A portable device for measuring a coefficient of static friction has a base plate, a voice coil motor having an output shaft, an actuator member fixed to the output shaft, a photosensor electrically connected to the actuator member, a cell electrically connected to the voice coil motor and the photosensor, a measurement button, a display device, and a switching device which is connected to the measurement button.

20 Claims, 7 Drawing Sheets

$$\mu s = W\sin\theta / W\cos\theta = \tan\theta$$

FIG. 11

$$\mu s = W\tan\theta / W = \tan\theta$$

PORTABLE DEVICE FOR MEASURING A COEFFICIENT OF STATIC FRICTION

BACKGROUND OF THE INVENTION

The present invention relates in general to a measuring device for static friction, and more particularly to a portable device for measuring coefficient of a static friction of an article which permits an easy measurement of coefficient of a static friction of a surface of an article.

In the conventional friction measurement device, it has been required that a small specimen be made of exactly the same material as that of an article to be measured and that this specimen be set in position with respect to the friction measurement device. Further, there is an additional problem that the conventional friction measurement device is relatively large in size and generally installed in a laboratory or the like and, therefore, one is unable to carry or move the friction measurement device out of the laboratory to a place where the article to be measured is positioned. In addition to the above, the specimen made of exactly the same material as the article to be measured must be transported to the position where the measurement device is installed, which needs substantial labor and difficulty.

As described above, the conventional friction measurement device always requires moving the specimen to the device and further the device itself is of a large-size and installed in the predetermined position and, therefore, it is impossible to immediately obtain, at the very position of the articles, the data of the frictional coefficient of articles to be measured. Further, when a frictional coefficient is needed in the case of a floor surface of flooring (a floor-covering surface) or a lane surface of bowling lanes which are coated with wax, it is quite difficult to reproduce the specimen thereof and, thus, it is difficult to conduct a measurement of a frictional coefficient.

SUMMARY OF THE INVENTION

An object of the present invention is to provide a friction measurement device which is small sized and portable to a site where an article to be measured is located and which can measure a frictional coefficient.

Another object of the present invention is to provide a friction measurement device which permits an easy measurement of a frictional coefficient without preparation of a specimen.

According to the present invention, there is provided a portable device for measuring a coefficient of friction comprising: a voice coil motor, a sensor for detecting a movement of an output shaft of said voice coil motor, a detector for detecting an electric current supplied to said voice coil motor, a converter for converting an electric current value detected by said detector into a coefficient of static friction, wherein when an article to be measured is pushed and moved by a movement of said output shaft of said voice coil motor, an electric current is supplied to said voice coil to thereby obtain a coefficient of static friction.

In the structure described above, a display for displaying data of the obtained coefficient of static friction can be provided.

Further, a measurement button for starting the measurement can be provided so that when the measurement button is placed in an ON state, the output shaft of the voice coil motor is moved forward to push the article to be measured.

In another mode of the invention, there is provided a portable device for measuring a coefficient of static friction comprising: a voice coil motor, a photosensor, a display for displaying a coefficient of static friction of an article to be measured, a switching device for supplying an electric power to said voice coil motor, a button for starting a measurement of the article, and a power source, wherein an actuator member is connected to an output shaft of the voice coil motor so that a movement of the actuator member is detected, and wherein above-described voice coil motor, photosensor, display, measurement button, and power source are electrically connected by a base plate in a body member having a cover, so that the output shaft of the voice coil motor extends out of the body member.

According to another mode of the invention, there is provided a portable device for measuring a coefficient of static friction in which: a voice coil motor is mounted on a base plate having an opening at its lower end, a friction plate is detachably connected to a lower end of a slidable shaft fitted to an output shaft of the voice coil motor, the friction plate is movable back and forth in the opening so that the friction plate extends downwardly from a lower end of the base plate and a display device for displaying a coefficient of static friction of an article to be measured and a measurement button for starting a measurement and a switch for selectively supplying an electric power to the voice coil motor are all mounted on a cover fitted on the base plate, a photosensor for detecting a movement of the output shaft of the voice coil motor is mounted on a sensor fixture member, and a cell mounted on the base plate and the voice coil motor and the photosensor and the display and the switch are all electrically connected to each other.

In the present invention described above, the output shaft of the voice coil motor is free when the power source is in the OFF state and when the power source is in the ON state to supply an electric current, the output shaft is retracted to a position of starting the measurement. Then, when a measurement button is pushed in to start the measurement, the voice coil motor is gradually supplied with an electric current to move the output shaft forward. At the very moment when the output shaft contacts a surface of an article for measurement to thereby start to move the article, or otherwise, when a friction plate which is attached to the output shaft through a slidable shaft starts to move, a value of the electric current at this moment is detected and thereafter the detected value is computed and displayed as a coefficient of static friction on a display. Thus, a frictional coefficient of the article can be obtained.

PREFERRED EMBODIMENTS OF THE INVENTION

Figure 1:
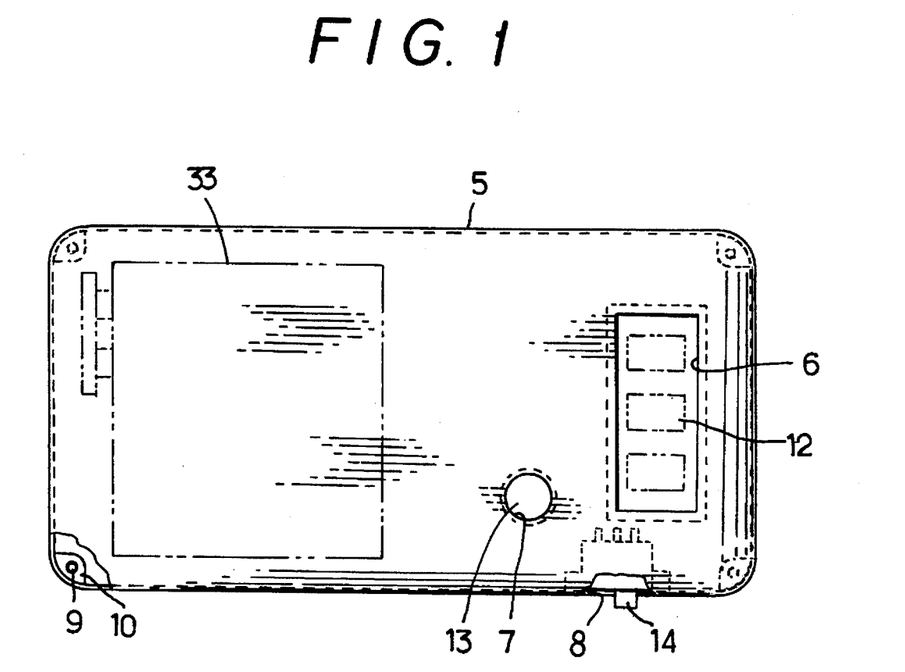
FIG. 1 is a plan view of a cover which is a component of a friction measurement device according to the present invention.
Figure 2:
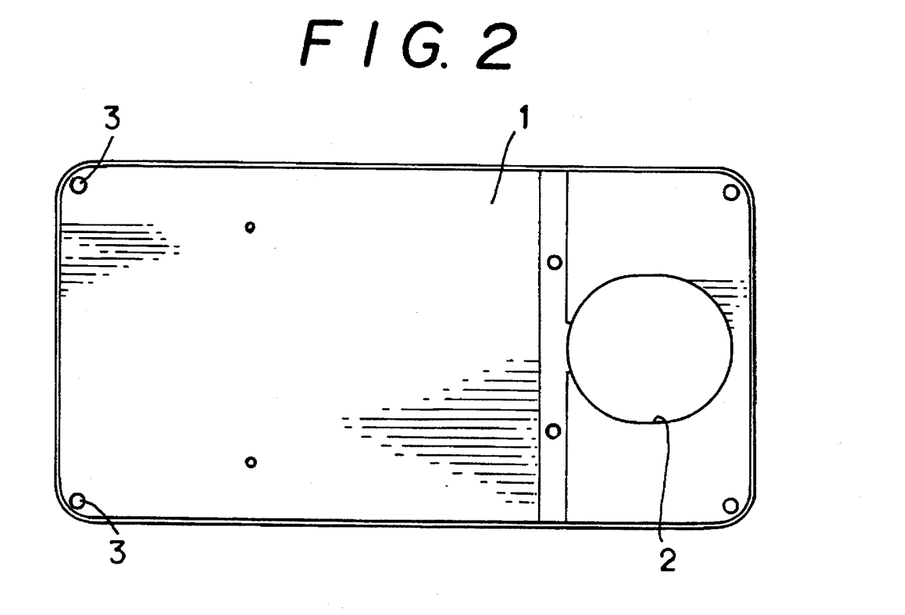
FIG. 2 is a plan view of a base plate which is another component of the friction measurement device according to the present invention.

A first embodiment of the invention will be described with reference first to FIGS. 1 and 2 wherein reference numeral 1 in FIG. 2 represents a base plate and a reference numeral 5 in FIG. 1 a cover. The base plate 1 has an oval or substantially circular opening 2 near an end portion, and screw holes 3 at the corners thereof. The cover 5 which is to be adapted to the base plate 1 has a window 6 for mounting thereon a display device 12 such as a LED (light emitting diode) display consisting, for example, of three digits each having seven segments, and a circular hole 7 for mounting thereon a measurement button 13. The cover 5 has on its side portion a hole for receiving an ON/OFF switch 14 for the electric power source (not shown). At the bottom corners, connecting members 10 each having a threaded hole 9 for engagement with a bolt (not shown) are provided so that the bolt is engaged with the screw hole 3 of the base plate.

In FIGS. 3 to 6, a voice coil (VC) motor 18 is disposed on the base plate 1. The voice coil motor 18 has a housing 16 and a sensor fixing member 25 at a front end of the housing 16, and a photosensor 17 is mounted on the sensor fixing member 25. If necessary, the sensor fixing member 25 may be disposed directly on the base plate 1. The voice coil motor 18 has an output shaft 19 and a slidable shaft 20 which extends from, at right angles, an end of the output shaft 19 so that the slidable shaft 20 is secured to the end of the output shaft 19. The slidable shaft 20 is connected at its lower end to a movable fixture plate 21 of a circular shape. Further, a frictional plate 22 of a circular configuration is removably connected to the lower end of the movable fixture plate 21. The friction plate 22 serves as the mechanical interface between the friction measurement device and the surface of the article to be measured.

A rubber gasket 24 is fitted to a groove 23 formed around the outer circumference of the friction plate 22, thereby preventing the outer edge of the friction plate 22 from collision against an inner surface of the opening portion 2 of the base plate 1, thereby preventing the generation of noise by the present device. The friction plate 22 is attached to the lower end of the slidable shaft 20 which is attached to the end of the output shaft 19 of the voice coil motor 18 so that the friction plate 22 can move back and forth in the opening portion 2 provided on one side of the plate 1 with the slidable shaft 20 attached to the end of the output shaft 19 within a certain range of movement on. Specifically, the movement distance in this embodiment is about 4.0 mm which, however, can be selected as desired.

At the low end of the slidable shaft 20 which is secured to the end of the output shaft 19, the movable fixture member 21 is fixed thereto by means of a slidable bearing and an E-ring 32 so that an article to be measured receives the total weight of the movable fixture member 21 and the friction plate 22 fixed thereunder. The E-ring 32 stops the slidable bearing fitted on the slidable shaft 20, and the friction plate 22 is removably fitted to the movable fixture member 21 by screws. According to this construction, the friction plate 22 can be removed and cleaned when oil and/or dust adheres to the lower surface of the friction plate 22 attached under the movable fixture member 21 in the case of attaching the lower surface to an article to be measured, thereby preventing an error of the measured value. Furthermore, the friction plate 22 is easily removed and replaced from the movable fixture member 21 when the base of the friction plate 22 is damaged.

When the slidable shaft 20 moves longitudinally together with the output shaft 19, the actuator member 20a, which is disposed above the slidable shaft also moves concurrently, so that one end(back side) of the actuator member 20a, which is positioned in the slit provided in the middle of the photosensor 17 and which interrupts the light from the light-emitting portion in the slit, moves forward. When the light from the light-emitting portion enters the light-receiving portion, the photosensor 17 senses the light and the overall measurement is thereby effected.

Figure 3:
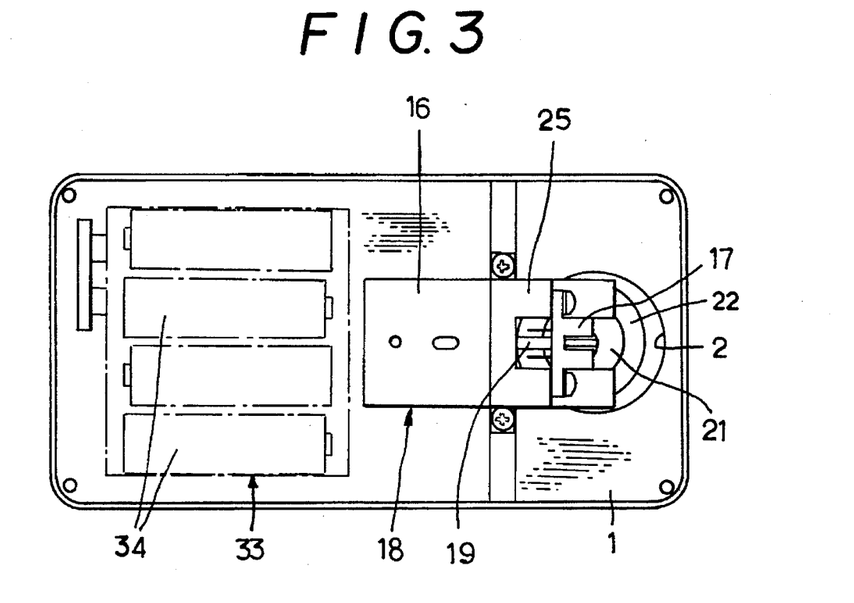
FIG. 3 is a plan view of an assembly of the friction measurement device showing that a voice coil motor and a friction plate are connected on the base plate.
Figures 4, 5:
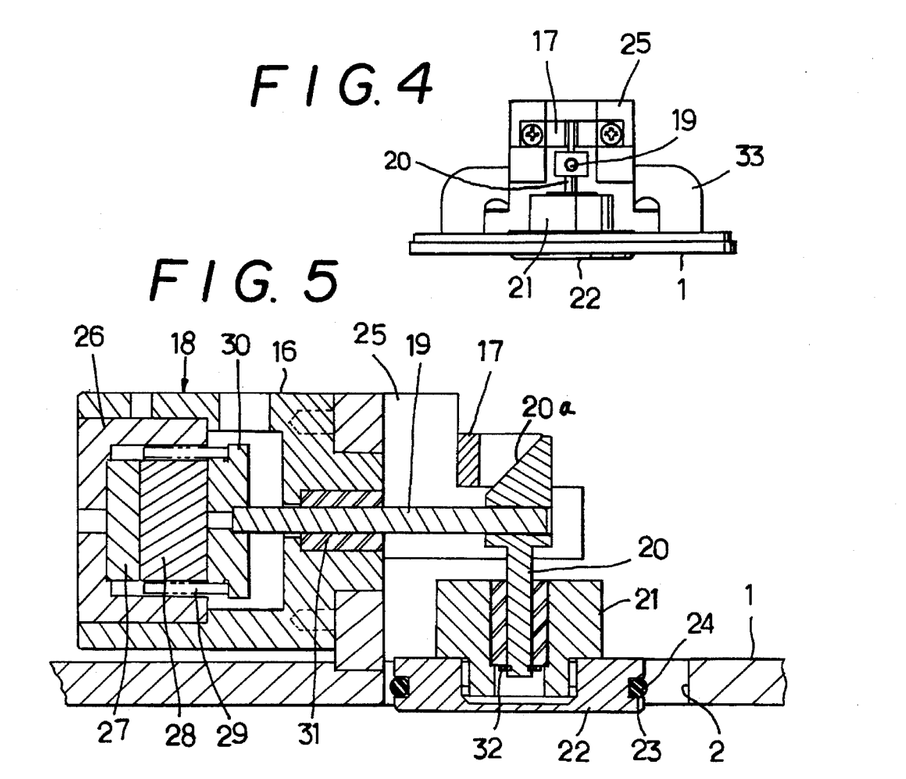
FIG. 4 is a side view of the assembly shown in FIG. 3.
FIG. 5 is a sectional view of the voice coil motor showing the positional relationship among the voice coil motor, its output shaft and the friction plate.

In FIGS. 3 and 4, a cell holder 33 is disposed on the base plate 1 and holds therein cells 34 such as a Ni-Cd (nickel-cadmium) cells or alkaline cell. The cell holder 33 is electrically connected to the cells 34, the switch 14 (FIG. 1), the display device 12, the photosensor 17, the measurement button 13 and the voice coil motor 18. If necessary, it will be possible to use an AC power source in place of the cells 34.

Figure 6:
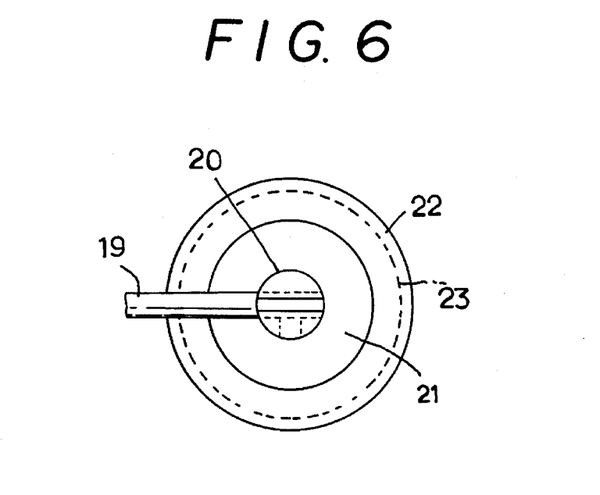
FIG. 6 is a plan view showing a relationship among the output shaft of the voice coil motor, a slidable shaft and friction plate.

In FIGS. 5 and 6, the voice coil motor 18 has a yoke 26 at the rear of the housing 16, a rare earth magnet 27 at the front portion of the yoke 26, a magnet holder 28 for holding the magnet 27, and a voice guide 30 having a coil 29 around the outer circumference of the magnet holder 28 in such a manner that the voice guide 30 can move back and forth in the yoke 26. The output shaft 19 is connected to the front portion of the voice guide 30 and extended forwardly, and a bearing 31 is disposed between the housing 16 and the output shaft 19.

Figure 7:
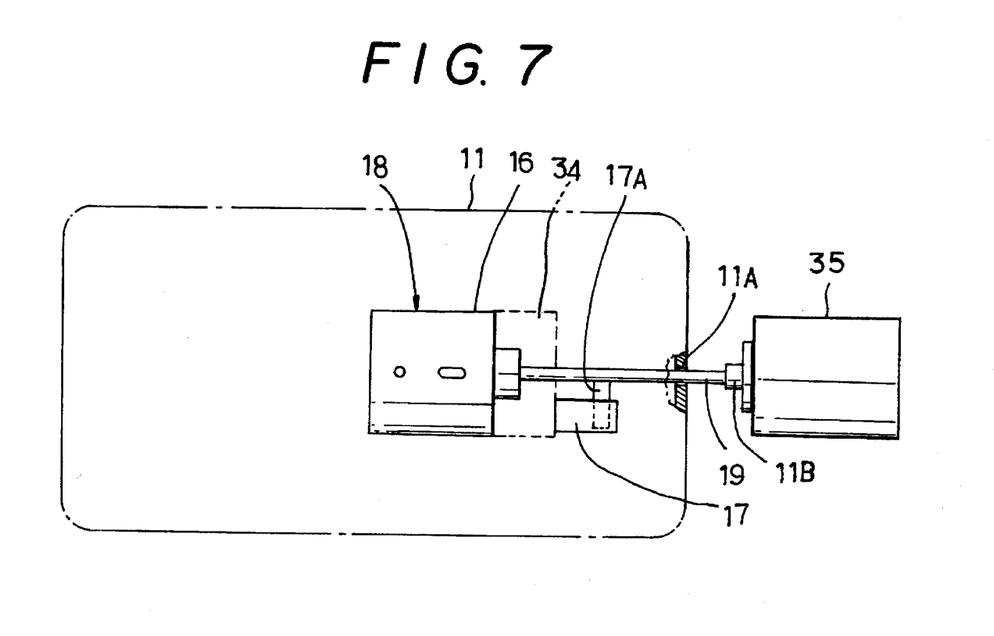
FIG. 7 is a partly cut-out plan view of the friction measurement device according to a second embodiment of the present invention.

In FIG. 7 showing a second embodiment of the present invention, the voice coil motor 18 which is housed in the device body 11 having the base plate 1 and the cover 5 has the output shaft 19 which is extended out of the body 11 through an opening 11A. On the end of the output shaft 19 is provided an attachment member 11B which has a recess or a flat surface on its end so that the attachment member can be adapted in accordance with the size and shape of the article to be measured. In the second embodiment illustrated in FIG. 7, the end of the output shaft 19 contacts the article 35 which is placed on a floor or a table, without using the friction plate 22 which is employed in the first embodiment shown in FIGS. 1–6, and the measurement button 13 is pushed to carry out the measurement of the friction.

It is also possible to measure a frictional coefficient by placing the end of the output shaft 19 in contact with the article 35 without using the attachment member 11B. In FIG. 7, an operational member or actuator 17A is disposed in the middle of the output shaft 19 and in a detectable range of the photosensor 17 which is fitted on a fixture member 34 fitted to the body 11 of the voice coil motor 18. Thus, when the actuator 17A is moved along with the output shaft 19 of the motor 18, the movement of the actuator 17A can be detected by the photosensor 17.

Figure 8:
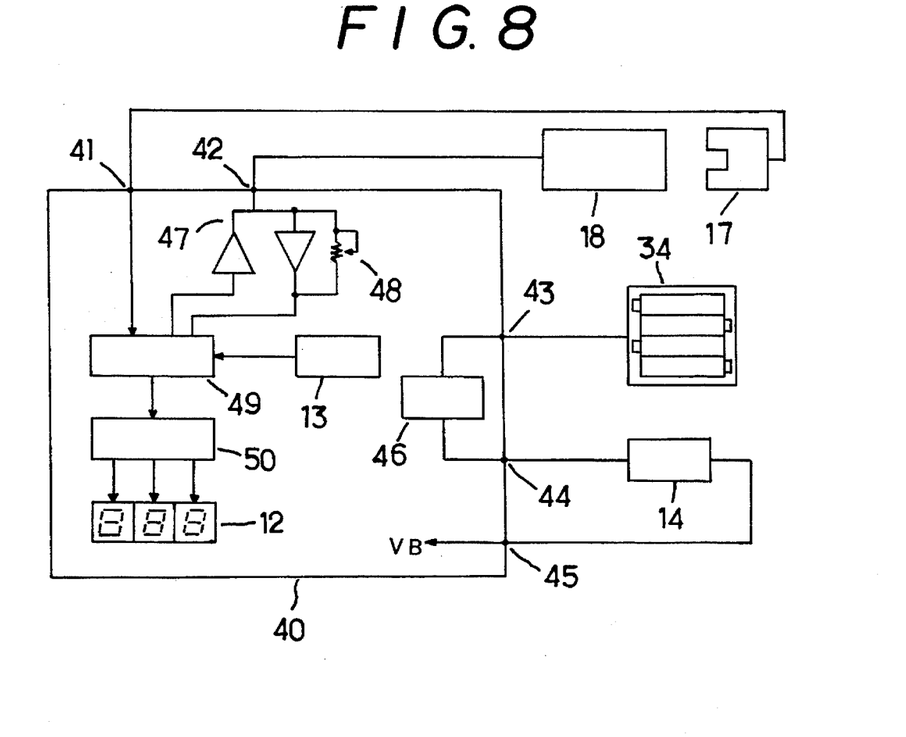
FIG. 8 is a diagram showing an electric circuit employed in the present invention.

With reference to FIG. 8, an electric circuit employable in the present invention will be described. In FIG. 8, the electric circuit 40 has terminals 41, 42, 43, 44, 45. The voice coil motor 18 and the photosensor 17 are electrically connected to the terminals 41 and 42, and the cells 34 are connected to the terminal 43. The other terminals 44 and 45 are connected to the ON/OFF switch 14 for the power source, and a regulator 46 is connected between the terminals 43 and 44. The voice coil motor 18 is connected to a controller 47 and a volume device 48 for adjusting the controller 47. The controller 47 which is connected to the terminals 41 and 42 is connected to a chip microprocessor (MPU) 49, and the microprocessor 49 is connected to the display device 12 such as a 7-segment LED display device having three digits through a decoder 50. Further, the microprocessor 49 is connected to the measurement button 13 for starting the measurement.

The microprocessor 49 is connected to the photosensor 17 through the terminal 41 so that the detection output of the photosensor 17 is fed to the microprocessor. Further, the microprocessor detects a value of an electric current which is supplied to the voice coil motor 18. If desired and/or necessary, the electric current can be detected by providing an ammeter at a desired place.

An operation of the friction measurement device of the present invention will be explained.

The output shaft 19 of the voice coil motor 18 is free when the power source is in its OFF state. When the switch is placed in its ON state to feed an electric current to the voice coil motor 18 and the display device 12, the output shaft 19 is retracted and set to the starting position of the measurement. When the measurement button 13 is then pushed to feed the electric current to the coil 29, the electric current is fed gradually to the voice coil motor 18 to thereby move the output shaft forward. At the time when the article 35 or the friction plate 22 starts to move, the movement is simultaneously detected by the photosensor 17. The value of the electric current which is supplied to the voice coil motor 18 at the very moment of the detection by the photosensor 17 is detected by the microprocessor 49. Based upon the detected electric current value, a thrust of the output shaft is, as described presently, calculated by the microprocessor 49 which then calculates a coefficient of static friction of the article to be measured from the data such as the generated thrust, thrust constant, etc. The calculated coefficient of static friction is then displayed by the display device 12. The calculation and processes by the microprocessor 49 are effected by predetermined programs which are stored in a ROM and the like.

Figure 10:
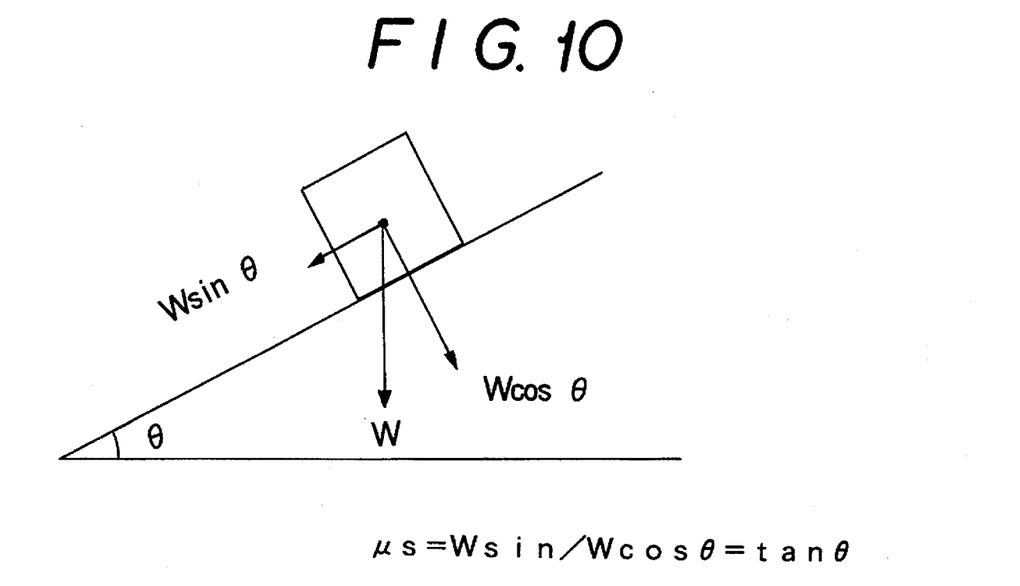
FIG. 10 is a diagram showing an operational principle of the frictional measurement device of the present invention.
Figure 11:
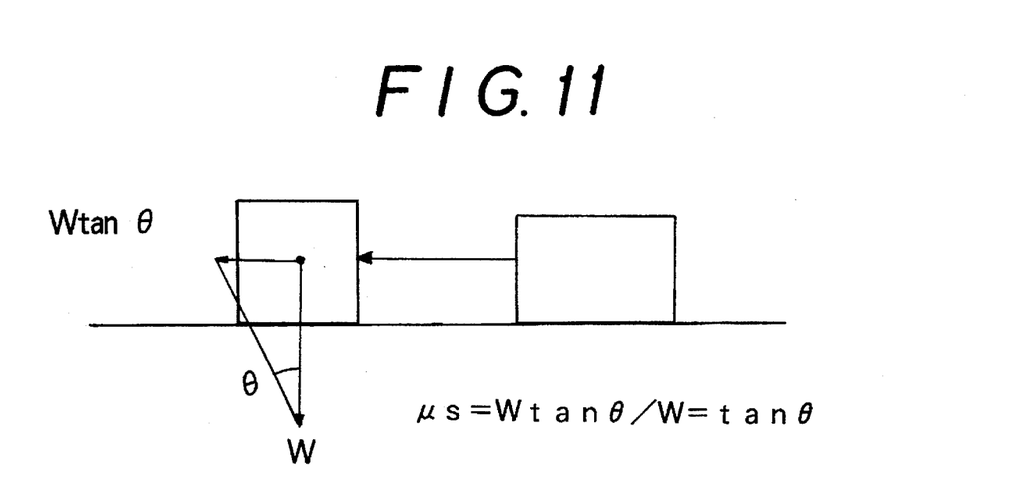
FIG. 11 is a diagram showing a measurement principle of the frictional measurement device of the present invention.

The measurement principle of the present invention will be described with reference to FIGS. 10 and 11. In FIG. 10, a small article is placed on a plate or a rod, and this plate is then gradually inclined to measure an angle θ of the inclination where the article starts to slide. This method of measurement can be made in accordance with the formulas (1) and (2) as set forth below to obtain a coefficient of static friction. In FIG. 11, an article is place on a horizontal plate and an electric current is gradually fed to the voice coil motor 18 so that the article starts to move. From generation of a thrust at the time of the start of movement of the article, a thrust constant represented by formula (3) is obtained from the formulas (1) and (2) to thereby to carry out the measurement of a coefficient of static friction.

Correlation among a coefficient of static friction, a thrust and a thrust constant is as set forth below.

coefficient of static friction ($\mu s$)=thrust (F)/friction plate weight (W) .... (1)

thrust F=thrust constant×electric current value .... (2)

thrust constant=constant of a thrust generated at the time of supplying an electric current (capacity of each voice coil motor) .... (3)

Weight of the friction plate=40.00 g

A generated thrust in case that a thrust constant is 0.35 g/mA is:

0.35 gf in case of 1 mA;

3.50 gf in case of 10 mA; and 35.00 gf in case of 100 mA.

Thus, a proportional relationship is found.

Figure 9:
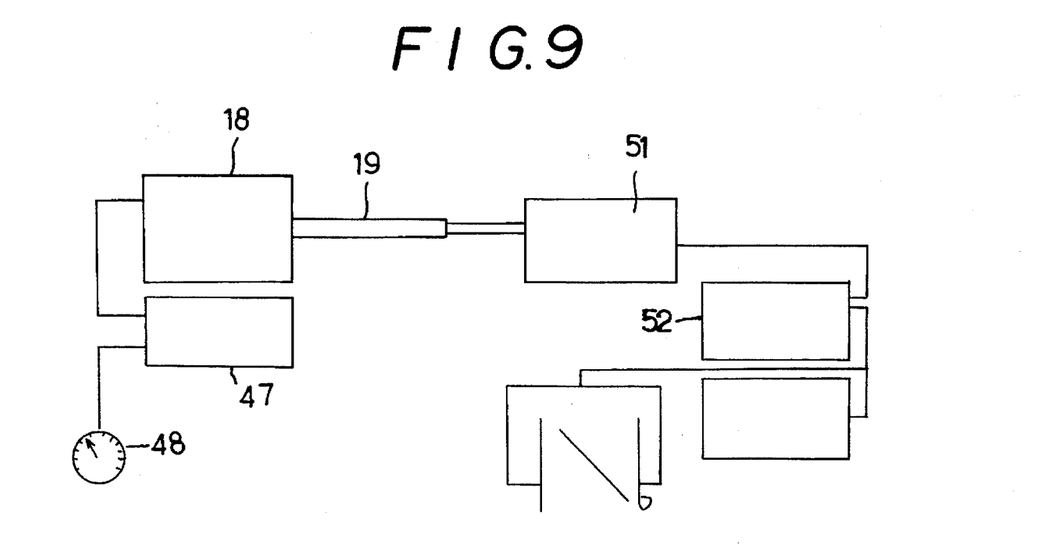
FIG. 9 is a diagram showing an adjustment of an output of the voice coil motor.

The thrust constant varies in accordance with properties of each voice coil motor 18 and, therefore, a constant is predetermined by a strain gage 51. In FIG. 9, reference numeral 52 represents a generally known strain amplifier. Further, a comparison between a value of electric current and a thrust is carried out by disposing horizontally a strain gage on the output shaft 19 of the voice coil motor 18 and gradually increasing an electric current value from 0 mA and then recording each thrust. By the correlation between the electric current value and the thrust, there is obtained a formula:

thrust/electric current value=assumed thrust (gf/mA)

Figure 12:
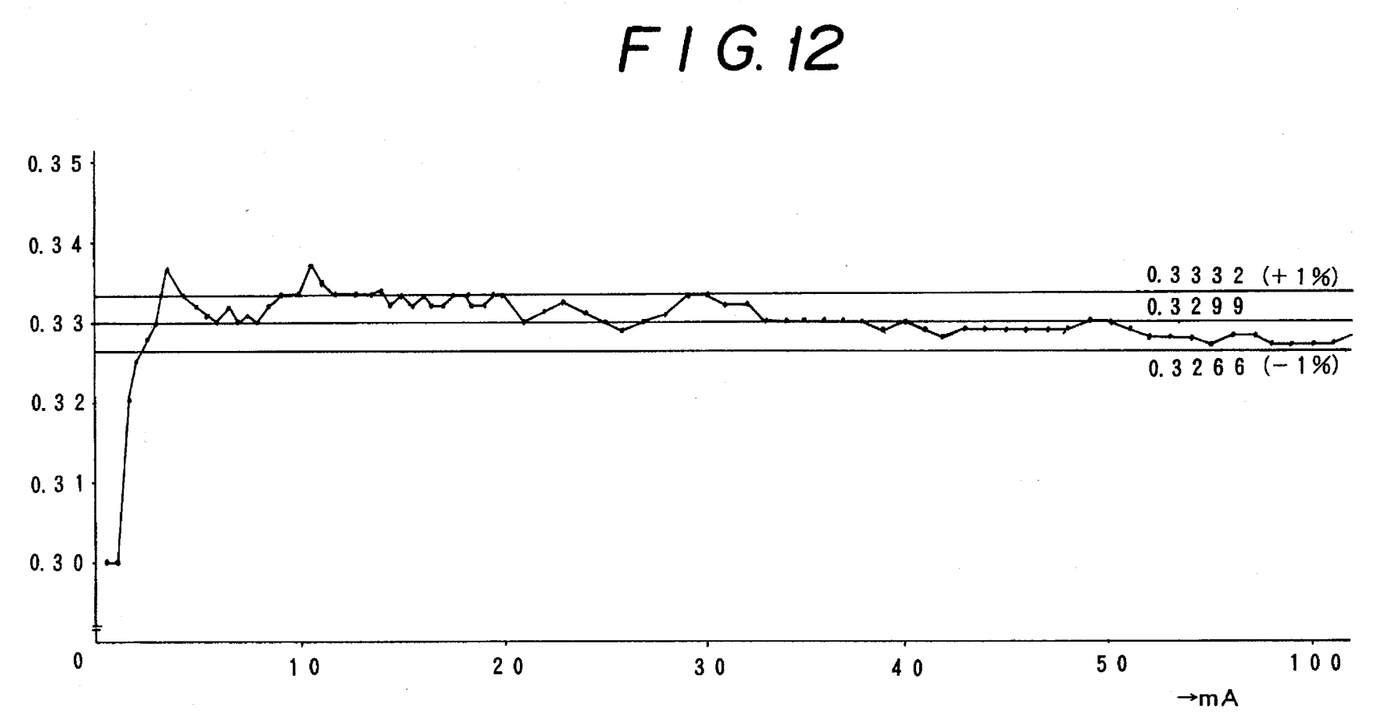
FIGS. 12 and 13 are graphs showing the relationship between an electric current value (mA) and a thrust (g).
Figure 13:
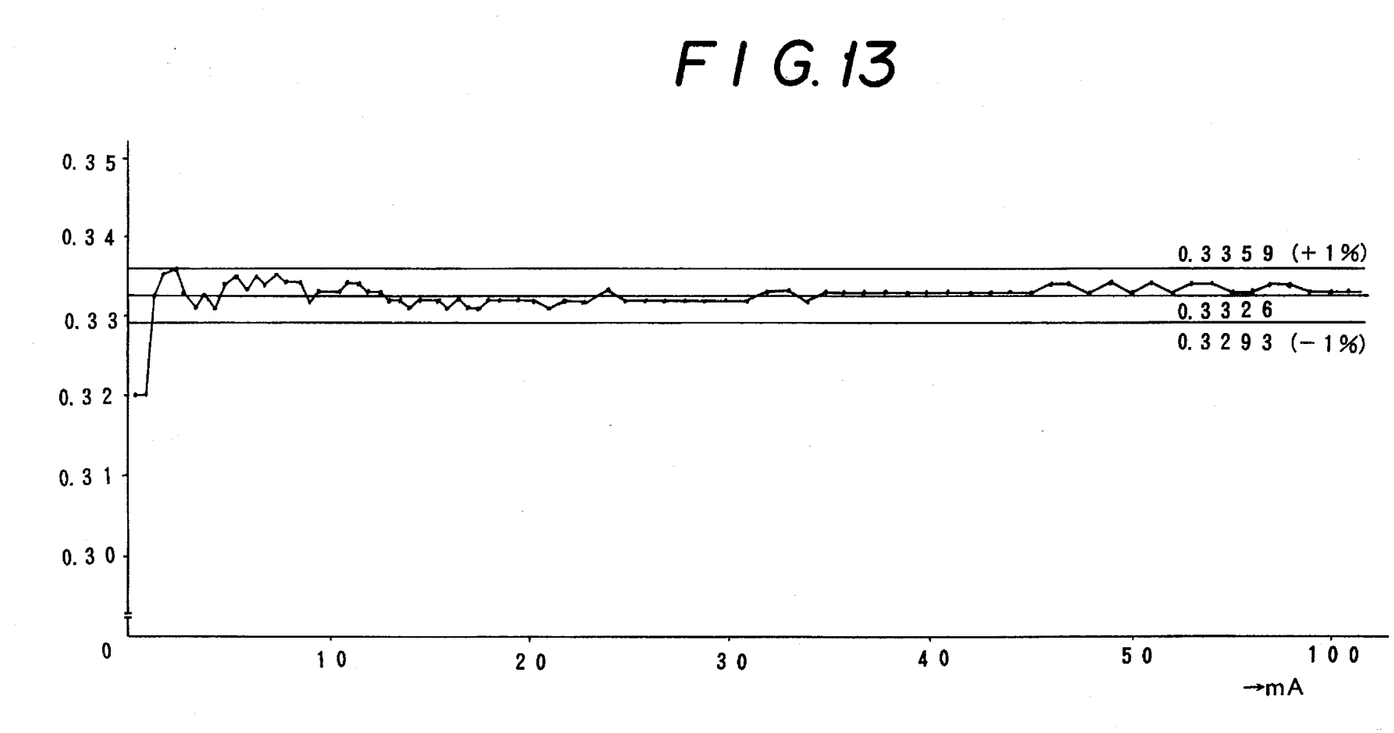

In the measurement, the rise of electric current value is of a digital method and divided into 255. Electric current values mA, thrusts g and assumed thrusts are shown in Table 1 and Table 2 which are shown by way of graphs in FIGS. 12 and 13. As shown by these tables and figures of the drawing, the values measured by the friction measurement device of the present invention are found in a predetermined range.

TABLE 1

| current value (mA) | thrust (g) | thrust constant | current value (mA) | thrust (g) | thrust constant |
|---|---|---|---|---|---|
| 0 | 0 | 0 | 31 | 10.30 | 0.332 |
| 0.5 | 0.15 | 0.30 | 32 | 10.62 | 0.332 |
| 1.0 | 0.30 | 0.30 | 33 | 10.90 | 0.330 |
| 1.5 | 0.48 | 0.320 | 34 | 11.23 | 0.330 |
| 2.0 | 0.65 | 0.325 | 35 | 11.55 | 0.330 |
| 2.5 | 0.82 | 0.328 | 36 | 11.88 | 0.330 |
| 3.0 | 0.99 | 0.330 | 37 | 12.20 | 0.330 |
| 3.5 | 1.18 | 0.337 | 38 | 12.53 | 0.330 |
| 4.0 | 1.34 | 0.335 | 39 | 12.85 | 0.329 |
| 4.5 | 1.50 | 0.333 | 40 | 13.20 | 0.330 |
| 5.0 | 1.66 | 0.332 | 41 | 13.48 | 0.329 |
| 5.5 | 1.82 | 0.331 | 42 | 13.78 | 0.328 |
| 6.0 | 1.98 | 0.330 | 43 | 14.13 | 0.329 |
| 6.5 | 2.16 | 0.332 | 44 | 14.48 | 0.329 |
| 7.0 | 2.31 | 0.330 | 45 | 14.80 | 0.329 |
| 7.5 | 2.48 | 0.331 | 46 | 15.13 | 0.329 |
| 8.0 | 2.64 | 0.330 | 47 | 15.45 | 0.329 |
| 8.5 | 2.82 | 0.332 | 48 | 15.80 | 0.329 |
| 9.0 | 3.00 | 0.333 | 49 | 16.15 | 0.330 |
| 9.5 | 3.16 | 0.333 | 50 | 16.48 | 0.330 |
| 10.0 | 3.33 | 0.333 | 55 | 18.08 | 0.329 |
| 10.5 | 3.54 | 0.337 | 60 | 19.70 | 0.328 |
| 11.0 | 3.68 | 0.335 | 65 | 21.33 | 0.328 |
| 11.5 | 3.84 | 0.334 | 70 | 22.95 | 0.328 |
| 12.0 | 4.00 | 0.333 | 75 | 24.55 | 0.327 |
| 12.5 | 4.16 | 0.333 | 80 | 26.20 | 0.328 |
| 13.0 | 4.33 | 0.333 | 85 | 27.85 | 0.328 |
| 13.5 | 4.49 | 0.333 | 90 | 29.45 | 0.327 |
| 14.0 | 4.67 | 0.334 | 95 | 31.10 | 0.327 |
| 14.5 | 4.82 | 0.332 | 100 | 32.70 | 0.327 |
| 15.0 | 5.00 | 0.333 | 105 | 34.38 | 0.327 |
| 15.5 | 5.15 | 0.332 | 110 | 36.03 | 0.328 |
| 16.0 | 5.32 | 0.333 | 115 | 37.65 | 0.327 |
| 16.5 | 5.48 | 0.332 | 120 | 39.30 | 0.328 |
| 17.0 | 5.65 | 0.332 | 130 | | |
| 17.5 | 5.83 | 0.333 | 140 | | |

TABLE 1-continued

| current value (mA) | thrust (g) | thrust constant | current value (mA) | thrust (g) | thrust constant |
|---|---|---|---|---|---|
| 18.0 | 6.00 | 0.333 | 150 | | |
| 18.5 | 6.14 | 0.332 | 160 | | |
| 19.0 | 6.30 | 0.332 | 170 | | |
| 19.5 | 6.49 | 0.333 | 180 | | |
| 20.0 | 6.66 | 0.333 | 190 | | |
| 21 | 6.94 | 0.330 | 200 | | |
| 22 | 7.29 | 0.331 | 210 | | |
| 23 | 7.64 | 0.332 | 220 | | |
| 24 | 7.94 | 0.331 | | | |
| 25 | 8.24 | 0.330 | | | |
| 26 | 8.56 | 0.329 | | | |
| 27 | 8.90 | 0.330 | | | |
| 28 | 9.27 | 0.331 | | | |
| 29 | 9.65 | 0.333 | | | |
| 30 | 9.99 | 0.333 | | | 0.3299 |

TABLE 2

| current value (mA) | thrust (g) | thrust constant | current value (mA) | thrust (g) | thrust constant |
|---|---|---|---|---|---|
| 0 | 0 | 0 | 31 | 10.30 | 0.332 |
| 0.5 | 0.16 | 0.320 | 32 | 10.65 | 0.333 |
| 1.0 | 0.32 | 0.320 | 33 | 11.00 | 0.333 |
| 1.5 | 0.50 | 0.333 | 34 | 11.30 | 0.332 |
| 2.0 | 0.61 | 0.335 | 35 | 11.66 | 0.333 |
| 2.5 | 0.84 | 0.336 | 36 | 11.99 | 0.333 |
| 3.0 | 1.00 | 0.333 | 37 | 12.32 | 0.333 |
| 3.5 | 1.16 | 0.331 | 38 | 12.66 | 0.333 |
| 4.0 | 1.33 | 0.333 | 39 | 12.99 | 0.333 |
| 4.5 | 1.49 | 0.331 | 40 | 13.33 | 0.333 |
| 5.0 | 1.67 | 0.334 | 41 | 13.66 | 0.333 |
| 5.5 | 1.84 | 0.335 | 42 | 14.00 | 0.333 |
| 6.0 | 2.00 | 0.333 | 43 | 14.32 | 0.333 |
| 6.5 | 2.18 | 0.335 | 44 | 14.66 | 0.333 |
| 7.0 | 2.34 | 0.334 | 45 | 14.99 | 0.333 |
| 7.5 | 2.51 | 0.335 | 46 | 15.34 | 0.334 |
| 8.0 | 2.67 | 0.334 | 47 | 15.68 | 0.334 |
| 8.5 | 2.84 | 0.334 | 48 | 16.00 | 0.333 |
| 9.0 | 2.99 | 0.332 | 49 | 16.34 | 0.334 |
| 9.5 | 3.16 | 0.333 | 50 | 16.67 | 0.333 |
| 10.0 | 3.33 | 0.333 | 55 | 18.35 | 0.334 |
| 10.5 | 3.50 | 0.333 | 60 | 20.00 | 0.333 |
| 11.0 | 3.67 | 0.334 | 65 | 21.70 | 0.334 |
| 11.5 | 3.84 | 0.334 | 70 | 23.35 | 0.334 |
| 12.0 | 4.00 | 0.333 | 75 | 25.00 | 0.333 |
| 12.5 | 4.16 | 0.333 | 80 | 26.65 | 0.333 |
| 13.0 | 4.32 | 0.332 | 85 | 28.40 | 0.334 |
| 13.5 | 4.48 | 0.332 | 90 | 30.05 | 0.334 |
| 14.0 | 4.64 | 0.331 | 95 | 31.65 | 0.333 |
| 14.5 | 4.81 | 0.332 | 100 | 33.30 | 0.333 |
| 15.0 | 4.98 | 0.332 | 105 | 34.95 | 0.333 |
| 15.5 | 5.14 | 0.332 | 110 | 36.65 | 0.333 |
| 16.0 | 5.30 | 0.331 | 115 | 38.30 | 0.333 |
| 16.5 | 5.47 | 0.332 | 120 | 39.95 | 0.333 |
| 17.0 | 5.63 | 0.331 | 130 | | |
| 17.5 | 5.80 | 0.331 | 140 | | |
| 18.0 | 5.98 | 0.332 | 150 | | |
| 18.5 | 6.14 | 0.332 | 160 | | |
| 19.0 | 6.30 | 0.332 | 170 | | |
| 19.5 | 6.47 | 0.332 | 180 | | |
| 20.0 | 6.64 | 0.332 | 190 | | |
| 21 | 6.96 | 0.331 | 200 | | |
| 22 | 7.30 | 0.332 | 210 | | |
| 23 | 7.64 | 0.332 | 220 | | |
| 24 | 7.98 | 0.333 | | | |
| 25 | 8.30 | 0.332 | | | |
| 26 | 8.62 | 0.332 | | | |
| 27 | 8.97 | 0.332 | | | |
| 28 | 9.30 | 0.332 | | | |
| 29 | 9.63 | 0.332 | | | |
| 30 | 9.97 | 0.332 | | | 0.3326 |

For example, a measurement was carried out by operating the portable friction measurement device on a sheet of paper, the photosensor 17 was actuated. When the friction plate 22 moved at a measured current of 100 mA assuming that the estimated thrust=0.35), then the calculated a coefficient of static friction (μs)=0.35×100 (generated thrust) gf/weight 40 g=0.875 (0.88).

According to the present invention, the friction measurement device of the present invention can be made with a compact configuration and can be used without using a specimen. Furthermore, it is not necessary that the measurement device be fitted to any other apparatus and a coefficient of friction can be immediately measured at the desired place. Besides the above, a static friction coefficient can be measured easily by moving the output shaft of the voice coil motor and the measurement can be conducted simply by pushing the measurement button so that the measured values are displayed on the display device. Thus, an accurate measurement can be assured by conducting the measurement several times and then obtaining an average value from the measurements.

What is claimed is:

1. A portable device for measuring a coefficient of static friction comprising:

a voice coil motor;

a sensor means for detecting a movement of an output shaft of said voice coil motor;

a detector means for detecting an electric current supplied to said voice coil motor;

a converter means for converting an electric current value detected by said detector means into a coefficient of static friction;

wherein when an article to be measured is pushed and moved by an movement of said output shaft of said voice coil motor, and electric current is supplied to said voice coil to thereby obtain a coefficient of static friction.

2. The portable device for measuring a coefficient of static friction according to claim 1, further comprising a display means for displaying data of the obtained coefficient of static friction.

3. The portable device for measuring a coefficient of static friction according to claim 1, further comprising a measurement button means for starting the measurement and for moving said output shaft of said voice coil motor forward to push the article to be measured when said measurement button means is placed in an ON state.

4. The portable device for measuring a coefficient of static friction according to claim 1, further comprising a power source which comprises at least one cell.

5. The portable device for measuring a coefficient of static friction according to claim 1, wherein said sensor is a photosensor.

6. The portable device for measuring a coefficient of static friction according to claim 2, further comprising a measurement button means for starting the measurement, and for moving said output shaft of said voice coil motor forward to push the article to be measured when said measurement button means is placed in an ON state.

7. The portable device for measuring a coefficient of static friction according to claim 2, further comprising a power source which comprises at least one cell.

8. The portable device for measuring a coefficient of static friction according to claim 3, further comprising a power source which comprises at least one cell.

9. The portable device for measuring a coefficient of static friction according to claim 6, further comprising a power source which comprises at least one cell.

10. The portable device for measuring a coefficient of static friction according to claim 2, wherein said sensor is a photosensor.

11. The portable device for measuring a coefficient of static friction according to claim 3, wherein said sensor is a photosensor.

12. The portable device for measuring a coefficient of static friction according to claim 4, wherein said sensor is a photosensor.

13. The portable device for measuring a coefficient of static friction according to claim 6, wherein said sensor is a photosensor.

14. The portable device for measuring a coefficient of static friction according to claim 7, wherein said sensor is a photosensor.

15. The portable device for measuring a coefficient of static friction according to claim 8, wherein said sensor is a photosensor.

16. The portable device for measuring a coefficient of static friction according to claim 9, wherein said sensor is a photosensor.

17. A portable device for measuring a coefficient of static friction comprising:

a voice coil motor, a photosensor, a display for displaying a coefficient of static friction of an article to be measured, a switch for supplying an electric power to said voice coil motor, a button for starting a measurement of the article; and a power source, wherein an actuator member is connected to an output shaft of said voice coil motor so that a movement of said actuator member is detected; and wherein said voice coil motor, photosensor, display device, measurement button, switch and power source are electrically connected by a base plate in a body member having a cover, so that said output shaft of said voice coil motor extends out of said body member.

18. A portable device for measuring a coefficient of static friction in which:

a voice coil motor is mounted on a base plate having an opening at its lower end;

a friction plate is detachably connected to a lower end of a slidable shaft fitted to an output shaft of said voice coil motor;

said friction plate is movable back and forth in said opening so that said friction plate extends downwardly from a lower end of said base plate;

a display for displaying a coefficient of static friction of an article to be measured, a measurement button for starting a measurement, and a switch for selectively supplying an electric power to said voice coil motor are mounted on a cover fitted on said base plate;

a photosensor for detecting a movement of said output shaft of said voice coil motor, said photosensor being mounted on a sensor fixture member; and at least one cell mounted on said base plate, said voice coil motor, said photosensor, said display and said switch being electrically connected to each other.

19. The portable device for measuring a coefficient of static friction according to claim 18, wherein said sensor fixture member is fitted to said base plate.

20. The portable device for measuring a coefficient of static friction according to claim 18, wherein said sensor fixture member is fitted to a housing of said voice coil motor.

* * * * *